United States Patent [19]

Weisman et al.

[11] Patent Number: 4,673,402

[45] Date of Patent: Jun. 16, 1987

[54] ABSORBENT ARTICLES WITH DUAL-LAYERED CORES

[75] Inventors: Paul T. Weisman; Dawn I. Houghton, both of Fairfield, Ohio; Dale A. Gellert, Aurora, Ind.

[73] Assignee: The Procter & Gamble Company, Cincinnati, Ohio

[21] Appl. No.: 895,526

[22] Filed: Aug. 11, 1986

Related U.S. Application Data

[63] Continuation of Ser. No. 734,426, May 15, 1985, abandoned.

[51] Int. Cl.$^4$ .............................................. A61F 13/16
[52] U.S. Cl. ................................... 604/368; 604/378
[58] Field of Search .............. 604/358, 359, 367, 368, 604/378, 379, 385.1, 394, 396; 428/281, 286, 287, 289

[56] References Cited

U.S. PATENT DOCUMENTS

| | | | |
|---|---|---|---|
| 4,501,587 | 2/1985 | Enloe | 604/385 |
| 4,540,454 | 9/1985 | Pieniak et al. | 156/622 |
| 4,573,987 | 3/1986 | Lamb, Jr. | 604/378 |
| 4,573,988 | 3/1986 | Pieniak et al. | 604/379 |
| 4,573,989 | 3/1986 | Karami et al. | 604/381 |
| 4,585,448 | 4/1986 | Enloe | 604/378 |
| 4,605,402 | 8/1986 | Iskra | 604/368 |

FOREIGN PATENT DOCUMENTS

| | | |
|---|---|---|
| EP-A-158,914 | 10/1985 | European Pat. Off. . |
| EP-A-160,572 | 11/1985 | European Pat. Off. . |
| EP-A-160,569 | 11/1985 | European Pat. Off. . |
| 52-99046 | 7/1977 | Japan . |
| 59-188418 | 12/1984 | Japan . |
| 2063683 | 6/1981 | United Kingdom . |

*Primary Examiner*—John D. Yasko
*Attorney, Agent, or Firm*—George W. Allen; Steven J. Goldstein; Richard C. Witte

[57] ABSTRACT

The present invention provides absorbent articles, such as disposable diapers, which utilize substantially water-insoluble hydrogel material to enhance the absorbent capacity of such articles. In these articles, the hydrogel material, combined in particulate form with hydrophilic fiber material, is primarily placed in a lower fluid storage layer of the absorbent core of the article. Such a fluid storage lower layer of the absorbent core is placed underneath an upper, preferably larger, fluid acquisition/distribution layer containing little or no hydrogel. This lower fluid storage layer is positioned in such a manner that at least about 75% of the hydrogel in the lower layer is found in the front two-thirds of the absorbent article and such that at least about 55% of the hydrogel in the lower layer is found in the front half of the absorbent article. Absorbent articles of this type make especially effective and efficient use of the hydrogel material and may also provide a diaper rash control benefit. Absorbent cores of the type utilized in such articles are also disclosed.

21 Claims, 1 Drawing Figure

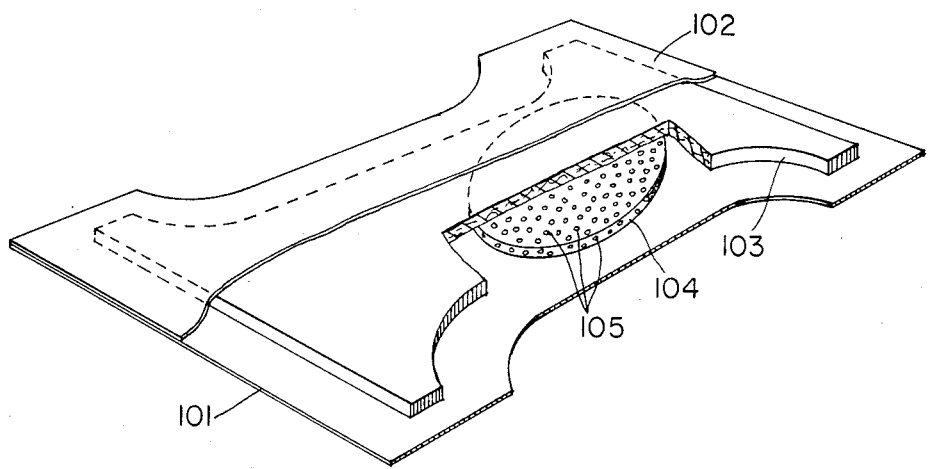

ABSORBENT ARTICLES WITH DUAL-LAYERED CORES

This is a continuation of application Ser. No. 734,426, filed on May 15, 1985, now abandoned.

FIELD OF THE INVENTION

This invention relates to absorbent articles using both hydrophilic fiber material and discrete particles of substantially water-insoluble hydrogel as absorbents. Absorbent articles of this type include disposable diapers, adult incontinence pads, sanitary napkins and the like.

BACKGROUND OF THE INVENTION

Water-insoluble hydrogels are polymeric materials which are c le of absorbing large quantities of fluids such as water and body wastes and which are further capable of retaining such absorbed fluids under moderate pressures. These absorption characteristics of water-insoluble hydrogels make such materials especially useful for incorporation into absorbent articles such as disposable diapers. Harper et al.; U.S. Pat. No. 3,669,103; Issued June 13, 1972 and Harmon; U.S Pat. No. 3,670,731; Issued June 20, 1972, for example, both disclose the use of hydrogel, i.e., "hydrocolloid," materials in absorbent products.

The effectiveness of fluid-absorbing hydrogel materials in disposable absorbent articles can be quite dependent upon the form, position and/or manner in which the hydrogel material is incorporated into the absorbent article. In some cases, for example, the effectiveness of hydrogel fluid absorption in absorbent articles can be adversely affected by a phenomenon called gel blocking. The term gel blocking describes a situation that occurs when a hydrogel particle, film, fiber, composite, etc. is wetted. Upon wetting, the surface of the hydrogel material swells and inhibits liquid transmission to the interior of the absorbent material. Wetting of the interior subsequently takes place via a very slow diffusion process. In practical terms, this means that absorption of fluid by the article is much slower than discharge of fluid to be absorbed, and failure of a diaper or sanitary napkin or other absorbent article may take place well before the hydrogel material in the absorbent article is fully saturated.

A number of prior art attempts have been made to improve the effectiveness of hydrogel materials in absorbent articles by minimizing gel blocking tendency. Thus, for Procter & Gamble; European Patent Application EP-A-No. 122,042; Published Oct. 17, 1984 discloses absorbent structures wherein hydrogel particles are dispersed in an air-laid web of hydrophilic fibers compressed to a particular density. Mesek et al.; U.S. Pat. No. 4,235,237; Issued Nov. 25, 1980 discloses an open absorbent network having particles of water-insoluble, water-swellable material spaced from each other within the network. Mazurak et al; U.S. Pat. No. 4,381,782; Issued May 3, 1983 discloses absorbent fibrous structures containing mixtures of hydrogel particles and surfactant-treated filler materials. Colgate Palmolive; U.K. Patent Specification No. 2,132,897A; Published July 18, 1984 discloses disposable absorbent articles containing a pad assembly having one or more surfaces coated with absorbent polymer in patterns designed to prevent gel blocking.

Other prior art attempts to improve the effectiveness of hydrogel materials in absorbent structures have involved particular arrangements for positioning hydrogel within the absorbent structure in discrete zones such as layers or pockets. The aforementioned EP-A-No. 122,042, for example, indicates that a hydrogel-containing absorbent structure can be positioned as a lower layer in a disposable absorbent product underneath an upper layer containing only hydrophilic fiber material. Mesek et al.; U.S. Pat. No. 4,102,340; Issued July 25, 1978 discloses an absorbent article having a hydrogel-containing batt positioned underneath a densified layer of fibrous material. Elias; U.S. Pat. No. 4,381,783; Issued May 3, 1983 discloses an absorbent article which includes an absorbent layer containing pockets of an admixture of hydrogel particles and discrete introfying particles. Holtman et al., U.S. Pat. No. 4,333,426; Issued June 8, 1982 and Holtman; U.S. Pat. No. 4,333,463; Issued June 8, 1982 both disclose absorbent structures containing reservoirs of superabsorbent particles positioned near one end of the structure at the void zone of the wearer. Personal Products Co.; European Patent Application EP-A-No. 108,637; Published May 16, 1984 describes thin absorbent products having a superabsorbent-containing absorbing layer and a wicking layer. Willington; U.K. Patent Specification No. 1,406,615; Published Mar. 15, 1973 discloses an absorbent pad having a urine-gelling agent incorporated only in the part of the pad "where it will be most effective."

Notwithstanding the various prior art attempts to improve the effectiveness of hydrogel materials in absorbent structures and products, there is a continuing need to identify hydrogel-containing absorbent articles wherein the hydrogel material is especially effective and efficient in performing its intended function of holding discharged body fluids without interfering with the acquisition and distribution of body fluids by and within the article. Hydrogel materials are generally significantly more expensive than readily available hydrophilic fiber materials (e.g. cellulose fibers). Accordingly it would be advantageous to provide articles wherein either absorbent capacity of the hydrogel-containing article can be improved or wherein a given absorbent capacity of an article can be maintained while reducing the amount of relatively expensive hydrogel material used. It would also be advantageous to provide articles wherein the fluid-storing hydrogel material does not adversely affect the ability of the absorbent article to quickly acquire discharged body fluids. It is therefore a primary objective of the present invention to provide absorbent articles which are especially effective and efficient in their use of hydrogel absorbent materials.

Another potential advantage which can be provided by certain hydrogel-containing disposable absorbent articles relates to the prevention or reduction of diaper rash. Diaper rash is a common form of irritation and inflammation of those parts of an infant's skin normally covered by a diaper. This condition is also referred to as diaper dermatitis, napkin dermatitis, napkin rash or nappy rash.

It is generally accepted that true "diaper rash" or "diaper dermatitis" is a condition which is commonly, in its most simple stages, a contact irritant dermatitis. The irritation of simple diaper rash results from extended contact of the skin with body waste. Diapers which catch and hold body waste in contact with the skin for long periods of time thus cause and/or aggravate diaper rash.

It has now been discovered that a primary cause of diaper rash is a particular set of conditions which arises as a result of prolonged contact of skin with mixtures of feces and urine. Activity of proteolytic and lipolytic fecal enzymes present in such a mixture is believed to be a major factor in producing skin irritation. Urine in contact with enzymes from feces can also result in production of ammonia which raises skin pH. This rise in skin pH, for example to levels of 6.0 and above, in turn increases that fecal proteolytic and lipolytic enzymatic activity which produces diaper rash.

The foregoing diaper rash model suggests that effective diaper rash control may be achieved by preventing mixtures of urine and feces from contacting diapered skin for any significant length of time. Prior art disposable diaper structures have not in general been designed to eliminate mixing of discharged urine and feces. It is, accordingly, a secondary objective of the present invention to provide absorbent articles such as diapers which hold discharged urine and feces in separate locations within the absorbent article and which might thereby prevent or reduce diaper rash caused by skin contact with urine-feces mixtures.

SUMMARY OF THE INVENTION

The present invention provides an absorbent article such as a diaper or incontinence pad which is suitable for absorbing body fluids in an especially effective and efficient manner and which may also prevent or reduce the incidence of diaper rash. Such an absorbent article comprises an elongated liquid impervious backing sheet, a relatively hydrophobic, liquid pervious topsheet and a layered, absorbent core positioned between the backing sheet and the topsheet.

The absorbent core comprises both an upper fluid acquisition/distribution layer which is preferably elongated and which consists essentially of hydrophilic fiber material and a lower fluid storage layer which consists essentially of a substantially uniform combination of hydrophilic fiber material and discrete particles of substantially water-insoluble hydrogel material.

The upper fluid acquisition layer has a density of from about 0.05 to 0.25 g/cm$^3$ and can optionally contain up to about 8% by weight of the upper layer of particles of substantially water-insoluble hydrogel material. The lower fluid storage layer has a density of from about 0.06 to 0.3 g/cm$^3$ and must contain from about 9% to 60% by weight of the lower layer of the hydrogel particles.

The lower fluid storage layer of the absorbent core has a top surface area which is from about 0.25 to 1.00 times the top surface area of the upper fluid acquisition/distribution layer. The lower fluid storage layer is further positioned relative to the upper fluid acquisition/distribution layer in a manner such that at least about 75% of the hydrogel material in the lower layer is found within the front two-thirds section of the article and such that at least about 55% of the total hydrogel material in the lower layer is found within the front half section of the article.

The present invention also relates to dual-layer absorbent cores, per se, of the type heretofore described, which can be employed in absorbent articles. Cores of the type utilized herein in absorbent articles, in addition to providing especially efficient and effective use of hydrogel absorbents, are also less likely to tear under the stress of wearing and loading.

BRIEF DESCRIPTION OF THE DRAWING

The drawing represents a cut-away view of a diaper structure having a dual-layer absorbent core.

DETAILED DESCRIPTION OF THE INVENTION .

The absorbent articles of the present invention can be manufactured in the configuration of wearable disposable products which are capable of absorbing significant quantities of water and body waste fluids such as urine, feces and menses. Thus such articles, for example, may be prepared in the form of disposable diapers, adult incontinence pads, sanitary napkins and the like.

The absorbent articles herein generally comprise three basic structural components. One such component is an elongated, liquid impervious backing sheet. On top of this backing sheet is placed an absorbent core which itself comprises two or more distinct layers. On top of this absorbent core is placed a relatively hydrophobic, water pervious topsheet. The topsheet is the element of the article which is placed next to the skin of the wearer.

Especially preferred absorbent articles of this invention are disposable diapers. Articles in the form of disposable diapers are fully described in Duncan and Baker, U.S. Pat. No. Re. 26,151, Issued Jan. 31, 1967; Duncan, U.S. Pat. No. 3,592,194, Issued July 13, 1971; Duncan and Gellert, U.S. Pat. No. 3,489,148, Issued Jan. 13, 1970; and Buell, U.S Pat. No. 3,860,003, Issued Jan. 14,1975; which patents are incorporated herein by reference. A preferred disposable diaper for the purpose of this invention comprises an absorbent core; a topsheet superposed or co-extensive with one face of the core, and a liquid impervious backsheet superposed or co-extensive with the face of the core opposite the face covered by the topsheet. The backsheet most preferably has a width greater than that of the core thereby providing side marginal portions of the backsheet which extend beyond the core. The diaper is preferably constructed in an hourglass configuration.

The elongated backing sheet (or backsheet) of the articles herein can be constructed, for example, from a thin, plastic film of polyethylene, polypropylene, or other flexible moisture impeding material which is substantially water impervious. Polyethylene, having an embossed caliper of approximately 1.5 mils, is especially preferred. For purposes of this invention, the backsheet is elongated if it is of unequal length and width in the unfolded, flat configuration.

The topsheet of the articles herein can be made in part or completely of synthetic fibers such as polyester, polyolefin, rayon, or the like, or of natural fibers such as cotton. The fibers are typically bound together by a thermal binding procedure or by a polymeric binder such as polyacrylate. This sheet is substantially porous and permits a fluid to readily pass therethrough into the underlying dual-layered absorbent core. The topsheet can be made more or less hydrophobic depending upon the choice and treatment of fiber and binder used in the construction thereof. The topsheets used in the articles of the present invention are relatively hydrophobic in comparison with the absorbent core of said articles. Topsheet construction is generally disclosed in Davidson, U.S. Pat. No. 2,905,176, Issued Sept. 22, 1959; Del Guercio, U.S. Pat. No. 3,063,452, Issued Nov. 13, 1962; and Holliday, U.S. Pat. No. 3,113,570, Dec. 10, 1963, which patents are incorporated herein by reference.

Preferred topsheets are constructed from polyester, rayon, rayon/polyester blends or polypropylene.

An absorbent core, which itself comprises two or more distinct layers, and which is preferably flexible, is positioned between the elongated backing sheet and the topsheet to form the absorbent articles herein. This core essentially comprises both an upper fluid acquisition/distribution layer and a lower fluid storage layer. It should be understood that for purposes of this invention these two types of layers refer merely to the upper and lower zones of the absorbent core and are not necessarily limited to single layers or sheets of material. Thus both the fluid acquisition/distribution layer and the fluid storage layer may actually comprise laminates or combinations of several sheets or webs of the requisite type of materials as hereinafter described. Thus as used herein, the term "layer" includes the terms "layers" and "layered."

One essential element of the absorbent core is an upper fluid acquisition/distribution layer which consists essentially of hydrophilic fiber material. This fluid acquisition/distribution layer serves to quickly collect and temporarily hold discharged body fluid. Since such fluid is discharged in gushes, the upper acquisition/distribution layer must be able to quickly acquire and transport fluid by wicking from the point of initial fluid contact to other parts of the acquisition/distribution layer. In the context of the present invention, it should be noted that the term "fluid" means "liquid."

Various types of hydrophilic fiber material can be used in the upper fluid acquisition/distribution layer of the core. Any type of hydrophilic fiber which is suitable for use in conventional absorbent products is also suitable for use in the upper layer of the core of the present absorbent articles. Specific examples of such fibers include cellulose fibers, rayon, and polyester fibers. Other examples of suitable hydrophilic fibers are hydrophilized hydrophobic fibers, such as surfactant-treated or silica-treated thermoplastic fibers. Also, fibers which do not provide webs of sufficient absorbent capacity to be useful in conventional absorbent structures, but which do provide good wicking properties, are suitable for use in the upper layer of the absorbent core of the present invention. This is so because the primary purpose of the upper layer of the core is to acquire and distribute fluid which has passed through the topsheet. Wicking properties of the fibers in the upper layer are thus of primary importance. For reasons of availability and cost, cellulose fibers, in particular wood pulp fibers, are preferred.

As indicated the primary function of the upper layer of the absorbent core is to receive fluids passing through the relatively hydrophobic, water pervious topsheet and to transport such fluids to other areas of the upper layer and eventually on to the fluid-holding, hydrogel-containing lower fluid storage layer of the core. The upper acquisition/distribution layer of the core can thus be substantially free of hydrogel material. Alternatively, the upper acquisition/distribution layer can contain small amounts of hydrogel material in particle form as hereinafter described. Thus the upper layer can, for example, contain up to about 8%, and preferably no more than about 6%, by weight of the upper layer of hydrogel particles. In some instances, the presence of hydrogel particles in the fluid acquisition/distribution layer can actually serve to maintain the density of the upper layer within the optimum range to promote fluid distribution. The specific type of hydrogel optionally used in the upper layer does not have to be the same as the hydrogel type essentially employed in the lower layer.

The shape, size and character, including capillarity (e.g., density), of the upper fluid acquisition/distribution layer of the articles herein is of some importance in determining the effectiveness of the resulting absorbent articles in absorbing discharged body fluids. As indicated, the upper absorbent layer of the core is preferably elongated. For purposes of this invention, this means that the upper layer, like the backing sheet, is elongated if it is of unequal length and width in the unfolded, flat configuration. The upper layer in the unfolded configuration can be of any desired shape, for example, rectangular, trapezoidal, oval, oblong or hourglass-shaped. The shape of the upper fluid acquisition/distribution layer of the core will frequently define the general shape of the resulting absorbent article.

The upper fluid acquisition/distribution layer will generally have a density of from about 0.05 to 0.25 $g/cm^3$. The basis weight of the upper layer of the absorbent core will typically range from about 0.015 to 0.1 $g/cm^2$. Density values are calculated from basis weight and layer caliper measured on newly unpacked, unfolded and dissected diapers. Caliper is measured under a "gentle" load of 10 grams/$cm^2$. Density and basis weight values include the weight of hydrogel particles, if present.

In preferred embodiments of the present invention the upper fluid acquisition/distribution layer of the core will be hourglass-shaped and will be of substantially uniform density within the range of from about 0.07 to 0.14 $g/cm^3$. Preferably, the upper fluid acquisition/distribution layer of the core will have a basis weight ranging from about 0.03 to 0.06 $g/cm^2$.

The upper layer of the absorbent core can be prepared in any conventional manner suitable for realizing a web of hydrophilic fiber material. Preferably the upper layer is formed by air-laying a stream of fiber material onto a screen until a web of the desired basis weight is formed. Such a web can subsequently be densified if necessary. Alternatively the upper fluid acquisition/distribution layer can comprise several layers of web material or can comprise, for example, a laminate or stack of tissue paper, provided such a layered structure, e.g., laminate, is of the requisite density hereinbefore set forth.

The lower fluid storage layer of the absorbent core of the articles herein consists essentially of a substantially uniform combination of hydrophilic fiber material and particular amounts of discrete particles of substantially water-insoluble, fluid-absorbing hydrogel material. The principal function of the fluid storage layer is to absorb discharged body fluid from the upper acquisition/distribution layer and retain such fluid under the pressures encountered as a result of the wearer's movements. Ideally the fluid storage lower layer will drain the upper layer of much of its aquired fluid load.

The hydrophilic fibers in the lower fluid storage layer can be of the same type as those hereinbefore described for use in the upper fluid acquisition/distribution layer. As in the upper layer, cellulose fibers, and especially wood pulp fibers and wood pulp tissue, are preferred.

In addition to hydrophilic fiber material, the lower fluid storage layer of the absorbent core of the articles herein also essentially contains discrete particles of substantially water-insoluble hydrogel material. Such hydrogel materials are inorganic or organic compounds capable of absorbing fluids and retaining them under moderate pressures.

Suitable hydrogels can be inorganic materials such as silica gels or organic compounds such as cross-linked polymers. Cross-linking may be by covalent, ionic, van der Waals, or hydrogen bonding. Examples of hydrogel polymers include polyacrylamides, polyvinyl alcohol, ethylene maleic anhydride copolymers, polyvinyl ethers, hydroxypropyl cellulose, carboxymethyl cellulose, polyvinyl morpholinone, polymers and copolymers of vinyl sulfonic acid, polyacrylates, polyacrylamides, polyvinyl pyridine and the like. Other suitable hydrogels are those disclosed in Assarsson et al., U.S. Pat. No. 3,901,236, Issued Aug. 26, 1975, the disclosure of which is incorporated herein by reference. Particularly preferred hydrogel polymers for use in the absorbent core are hydrolyzed acrylonitrile grafted starch, acrylic acid grafted starch, polyacrylates, and isobutylene maleic anhydride copolymers, or mixtures thereof.

Processes for preparing hydrogels are disclosed in Masuda et al., U.S. Pat. No. 4,076,663, Issued Feb. 28, 1978; in Tsubakimoto et al., U.S. Pat. No. 4,286,082, Issued Aug. 25, 1981; and further in U.S. Pat. Nos. 3,734,876, 3,661,815, 3,670,731, 3,664,343, 3,783,871, and Belgian Patent No. 785,850, the disclosures of which are all incorporated herein by reference.

Hydrogel material optionally found in the upper fluid acquisition/distribution layer and essentially found in the lower fluid storage layer of the absorbent cores herein is used in the form of discrete particles. Hydrogel particles can be of any desired shape, e.g., spherical or semi-spherical, cubic, rod-like, polyhedral, etc. Shapes having a large greatest dimension/smallest dimension ratio, like needles, flakes and fibers, are also contemplated for use herein. Conglomerates of hydrogel particles may also be used.

Although the hydrogel-containing layers are expected to perform well with hydrogel particles having a particle size varying over a wide range, other considerations may preclude the use of very small or very large particles. For reasons of industrial hygiene, average particle sizes smaller than about 30 microns are less desirable. Particles having a smallest dimension larger than about 2 mm may also cause a feeling of grittiness in the absorbent article, which is undesirable from a consumer aesthetics standpoint. Furthermore, rate of fluid absorption is affected by hydrogel particle size. Larger particles have very much reduced rates of absorption. Preferred for use herein are hydrogel particles having an average particle size of from about 50 microns to about 1 mm. "Particle Size" as used herein means the weighted average of the smallest dimension of the individual particles.

The relative amount of hydrophilic fiber material and hydrogel particles used in the lower fluid storage layer of the absorbent cores of the articles herein can be most conveniently expressed in terms of a weight percentage of the lower layer. The lower fluid storage layer of the absorbent cores herein must contain from about 9% to 60%, preferably from about 15% to 40%, by weight of the lower layer of hydrogel material. This concentration of hydrogel material can also be expressed in terms of a weight ratio of hydrogel to fiber. These ratios may range from about 9:91 to about 60:40. For most commercially available hydrogels the optimum hydrogel/fiber ratio is in the range of from about 9:91 to about 50:50. Based on a cost/performance analysis, hydrogel/fiber ratios of from about 20:80 to about 33:67 are preferred for use in the lower fluid storage layer.

The density of the hydrogel-containing lower fluid storage layer of the absorbent core can be of some importance in determining the absorbent properties of the resulting absorbent article. The density of the lower fluid storage layer will generally be in the range of from about 0.06 to about 0.3 g/cms$^3$, and more preferably within the range of from about 0.09 to about 0.18 g/cm$^3$. Typically the basis weight of the lower fluid storage layer can range from about 0.02 to 0.12 gm/cm$^2$. As with the upper layer, density values for the lower layer are calculated from basis weight and layer caliper measured on newly unpacked, unfolded and dissected articles. Caliper is measured under a "gentle" load of 10 grams/cm$^2$. Density and basis weight values include the weight of the hydrogel particles.

In a preferred embodiment of the present invention, the lower fluid storage layer will comprise an intimate admixture of hydrophilic fiber material and hydrogel particles with the hydrogel particles preferably being substantially uniformly distributed throughout a hydrophilic fiber matrix. Absorbent core lower fluid storage layers of this type can be formed by air-laying a dry mixture of hydrophilic fibers and hydrogel particles and densifying the resulting web. Such a procedure is described more fully in Procter & Gamble; European Patent Publication No. EP-A-No. 122,042; Published Oct. 17, 1984, incorporated herein by reference. As indicated in this reference, the webs formed by this procedure for use as the lower fluid storage layer will preferably comprise substantially unbonded fibers and will preferably have a moisture content of 10% or less.

Alternatively, the substantially uniform combination of hydrophilic fiber material and hydrogel particles used as the fluid storage layer of the core can comprise a laminate of at least two layers of dispersed hydrogel particles, overwrapped with and separated by sheets of hydrophilic fiber material such as tissue paper. Such a laminate structure is more fully described in Kramer, Young and Koch; U.S. Ser. No. 563,339; Filed Dec. 20, 1983, incorporated herein by reference.

It has been discovered that the hydrogel-containing lower fluid storage layer of the absorbent core need not be as large as the upper fluid acquisition/distribution layer of the core and can, in fact, have a top surface area (in the unfolded configuration) which is substantially smaller than the top surface area (unfolded) of the upper layer of the absorbent core. Generally, the top surface area of the lower fluid storage layer will range from 0.25 to 1.0 times that of the upper acquisition/distribution layer. More preferably the top surface area of the lower layer will be only from about 0.25 to 0.75, and most preferably from about 0.3 to 0.5, times that of the upper layer.

In accordance with the present invention, the lower fluid storage layer of the absorbent core must be placed in a specific positional relationship with respect to the backing sheet and/or the upper fluid acquisition/distribution layer in the absorbent article. More particularly, the hydrogel-containing lower fluid storage layer of the core must be positioned generally toward the front of the absorbent article so that hydrogel is most effectively located to drain and hold discharged body fluid from the upper acquisition/distribution layer. For purposes of the present invention, the front of the absorbent articles herein means the end of the absorbent article which is intended to be placed on the front of the wearer. Thus the lower fluid storage layer is to be placed in the vicinity of the point of discharge of body fluids.

The generally forward positioning of the lower hydrogel-containing fluid storage layer can be defined by specifying the percentage of total lower layer hydrogel which is found forward of particular points along the length of the absorbent article. Thus, in accordance with the present invention, the lower hydrogel-containing fluid storage layer is positioned relative to the upper elongated backing sheet and/or the acquisition/distribution layer such that (1) at least about 75% of the total hydrogel in the lower fluid storage layer is found within the front two-thirds section of the absorbent article, and (2) at least about 55% of the total hydrogel in the lower fluid storage layer is found within the front half section of the absorbent article.

More preferably, the lower fluid storage layer of the core is positioned relative to the elongated backing sheet and/or the upper acquisition/distribution layer such that at least about 90% of the total hydrogel in the lower layer is found in the front two-thirds section and at least about 60% of the total hydrogel in the lower layer is found in the front half section of the absorbent article. As noted, for purposes of the present invention, "sections" of the absorbent article can be defined by reference to top surface areas of the unfolded absorbent article found in front of a given point on the line which defines the length of the absorbent article.

For purposes of determining such lower layer positioning, the length of the absorbent article will be taken as the normal longest longitudinal dimension of the elongated article backing sheet. This normal longest dimension of the elongated backing sheet can be defined with respect to the article as it is applied to the wearer. When worn, the opposing ends of the backing sheet are fastened together so that these joined ends form a circle around the wearer's waist. The normal length of the backing sheet will thus be the length of the line running through the backing sheet from (a) the point on the edge of the backing sheet at the middle of the wearer's back waist, through the crotch, to (b) the point on the opposite edge of the backing sheet at the middle of the wearer's front waist.

In the usual instance wherein the upper layer of the absorbent core generally defines the shape of the absorbent article, the normal length of the elongated article backing sheet will be approached by the longest longitudinal dimension of the upper layer of the core. In such instances the positioning of the hydrogel-containing lower fluid storage layer can also be defined with respect to its location toward the front portion of the elongated upper fluid acquisition/distribution layer. However, in some applications (e.g. adult incontinence articles) wherein bulk reduction or minimum cost are important, the upper fluid acquisition/distribution layer would not take on the general shape of the diaper or incontinence structure. Rather the upper layer would be generally located to cover only the genital region of the wearer and could in this case have approximately the same top surface area as the lower fluid storage layer. In this instance both the upper fluid acquisition/distribution layer and the co-extensive lower fluid storage layer would be located toward the front of the article as defined by the backing sheet such that the requisite percentages of lower layer hydrogel would be found in the front two-thirds and front half sections respectively of the article.

The lower fluid storage layer of the absorbent core can be of any desired shape consistent with comfortable fit including, for example, circular, rectangular, trapezoidal or oblong, e.g., hourglass-shaped, dog-bone-shaped or oval. This lower fluid storage layer need not be physically separated from the upper fluid acquisition/distribution layer and can simply form a zone of high hydrogel concentration in a continuous web of fiber material. More preferably, however, the lower fluid storage layer of the absorbent core will comprise a separate web which can be used as an insert placed underneath a larger elongated upper acquisition/distribution layer. If desired, such an insert can be wrapped in a high wet strength envelope web such as tissue paper or a synthetic fine pore, e.g., nonwoven, material, to minimize the potential for hydrogel particles to migrate out of the insert layer. Another objective of such overwrapping is to desirably increase the in-use integrity of the dual layer core. Such a web can, in fact, be glued to the lower fluid storage insert layer. Suitable means for carrying out this gluing operation include the glue spraying procedure described in Minetola and Tucker; U.S. patent application Ser. No. 651,374, filed Sept. 17, 1984, incorporated herein by reference.

In preferred embodiments, the lower fluid storage layer of the absorbent core will be oblong. In especially preferred embodiments, an oblong insert overwrapped with spray-glued tissue will be employed.

One embodiment of an absorbent article according to the present invention comprises a disposable diaper such as that shown in the drawing. This drawing shows an hourglass-shaped diaper structure comprising a liquid impervious elongated sheet 101 and a hydrophobic water pervious topsheet 102. The absorbent core of the structure comprises two separate layers, i.e., an upper, hourglass-shaped, fluid acquisition/distribution layer 103 and a smaller, lower, oval insert fluid storage layer upper layer 103 comprises a web of air-laid cellulose fibers. The lower oval insert layer 104 comprises a web of cellulose fibers and contains discrete particles 105 of water-insoluble hydrogel distributed throughout this lower oval insert layer. The lower oval insert layer 104 positioned beneath the upper layer 103 toward the front of the diaper. In this manner at least 90% of the hydrogel material 105 in the lower insert layer 104 is found underneath the front two-thirds section of the upper layer 103 and at least 60% of this hydrogel material 105 is found underneath the front half section of the upper layer 103.

Another embodiment of the present invention relates to disposable, dual-layered absorbent cores per se which could be removably affixed, for example, to semi-disposable, reusable backsheets. Such cores are essentially the same as those described hereinbefore for use in the disposable absorbent articles of this invention. However, the positioning of the hydrogel in the lower fluid storage layer of such cores per se must be defined with respect to the front two-thirds and front half sections of the elongated upper fluid acquisition/distribution layer of the core. Thus the disposable cores per se utilize a lower fluid storage layer which is particularly positioned with respect to the upper fluid acquisition/distribution layer, or which has nonuniform hydrogel distribution therein, such that at least about 75% of the lower layer hydrogel is found in the front two-thirds section of the elongated core as defined by the length of upper layer and at least about 55% of the lower layer hydrogel is found in the front half section of the core as defined by the length of the elongated upper layer. Such disposable cores per se are preferably overwrapped or at least covered on top with liquid pervious topsheet material, e.g. tissue or non-woven material as hereinbefore described.

The absorbent articles and absorbent cores of the present invention, with their separate, particularly positioned zones containing fiber material and hydrogel material in particular amounts, are further illustrated by the following examples:

EXAMPLE I

A dual core disposable diaper is prepared utilizing a thermally bonded polypropylene topsheet, an hourglass-shaped primary core positioned below the topsheet, an oval insert positioned underneath the hourglass-shaped core and a fluid-impervious polyethylene backing sheet underneath the hourglass and insert core layers. The hourglass primary core comprises a major amount of cellulose wood pulp fiber and a minor amount of discrete particles of a starch acrylate hydrogel material. The oval insert layer comprises an air-laid mixture of cellulose wood pulp fibers and discrete particles of the same starch acrylate hydrogel material, present in a concentration significantly higher than in the hourglass layer. The oval insert is positioned toward the front of the hourglass such that 90% of the hydrogel material in the insert layer is found within the front two-thirds section of the disposable diaper and such that about 60% of the hydrogel in the insert is in the front half of the disposable diaper.

The two layers of the absorbent core of the diaper of this Example I are more completely described in Table I.

TABLE I

| Hourglass: | |
|---|---|
| Density | 0.22 g/cm$^3$ |
| Basis Weight | 0.033 g/cm$^2$ |
| Area | 643 cm$^2$ |
| % Hydrogel* | 2% by weight of hourglass |
| Insert | |
| Density | 0.22 g/cm$^3$ |
| Basis Weight | 0.05 g/cm$^2$ |
| Area | 221 cm$^2$ |
| % Hydrogel | 20% by weight of insert |
| Overall Hydrogel Content: | 8.1% by weight of total core |

*The hydrogel is Sanwet IM-1000, a starch acrylate material marketed by Sanyo Chemical Industries, Inc.

EXAMPLE II

Another dual core disposable diaper is prepared which is similar in construction to the Example I diaper. In this Example II article, the hourglass-shaped upper fluid acquisition/distribution layer of the absorbent core contains no hydrogel material at all so that all of the hydrogel in the diaper is found in the smaller oval insert layer. Again, the insert is positioned under the hourglass upper layer toward the front of the diaper such that 100% of the hydrogel material in the oval insert layer is found in the front two-thirds section of the diaper and such that about 60% of the hydrogel material in the oval insert is found in the front half of the diaper.

In this embodiment, the oval insert layer is overwrapped with spray glued high wet strength tissue to prevent particles of hydrogel from migrating from the oval insert core to other parts of the diaper. The disposable diaper of this example is more completely described in Table II.

TABLE II

| Hourglass: | |
|---|---|
| Dimensions | 15¼ × 10 in. (38.7 × 25.4 cm) |
| Area | 100 in$^2$ (645 cm$^2$) |
| Density | 0.18 g/cm$^3$ |
| Basis Weight | 0.19 g/in$^2$ (0.02945 g/cm$^2$) |
| Insert: | |
| Dimensions | 9 × 5¼ in. (22.9 × 13.3 cm) |
| Area | 41.3 in$^2$ (266 cm$^2$) |
| Density | 0.18 g/cm$^3$ |
| Basis Weight | 0.31 g/in$^2$ (0.048 g/cm$^2$) |
| Hydrogel* Content | 4.95 gm (36% by weight of insert) |

*The hydrogel is Sanwet IM-1000 marketed by Sanyo Chemical Industries, Inc.

EXAMPLE III

Fluid retention effectiveness of diapers such as described in Example I is determined by means of a leakage study. In such a leakage study, diapers are actually worn by infants. The infants are allowed to play in a nursery school-like setting during the test. The diapers are left on the infants until leakage occurs. In order to speed up the test, aliquots of synthetic urine are added at predetermined levels. The results of the leakage tests are reported in terms of average fluid capacity of the diaper at failure. By assuming that the cellulose fiber portion of the diaper core will hold about 4.0–4.5 grams of fluid per gram of fiber, it is possible to ca an approximate overall effective hydrogel capacity in terms of grams of fluid held per gram of hydrogel under simulated usage conditions.

The diapers tested in the leakage study were diapers of the Example I type having an hourglass-shaped primary absorbent core and an oval insert core positioned beneath the hourglass core and placed toward the front of the diaper. Density, basis weight and surface area of these two cores are as shown in Table 1. The amount of hydrogel in the hourglass and the insert is then varied as set forth in Table III.

TABLE III

| Diaper No. | 1 | 2 | 3 | 4 | 5 | 6 |
|---|---|---|---|---|---|---|
| % Hydrogel in Hourglass | 15 | 10 | 6 | 2 | 6 | 2 |
| % Hydrogel in Insert | 15 | 10 | 25 | 30 | 15 | 20 |
| Overall Hydrogel Content % | 15 | 10 | 12.5 | 11.6 | 9.1 | 8.1 |
| Results | | | | | | |
| Mean Capacity at Diaper Failure (g) | 226 | 195 | 244 | 234 | 209 | 231 |
| Overall Effective Hydrogel Capacity (g/g) | 21.8 | 21.6 | 30.3 | 29.4 | 28.6 | 39.4 |

The Table III data indicate that by placing most of the hydrogel particles in a forward positioned insert core, effective hydrogel capacity can be increased. Furthermore, it can be seen that diaper capacity for all of these diaper executions is not significantly different even though diapers 3, 4, 5 and 6 with the hydrogel mostly in the insert use a smaller total amount of hydrogel.

EXAMPLE IV

The diaper of Example II having no hydrogel in the primary upper layer is also tested in a leakage study. Performance of the Example II diaper was compared with that of a similar dual core diaper having hydrogel uniformly distributed throughout both an hourglass-shaped primary core and a smaller oval insert placed underneath the hourglass. Again measurements for overall diaper capacity at failure and hydrogel efficiency in terms of fluid held per gram of hydrogel were determined. Also determined was the extent of fluid wicking which occurs in the primary hourglass-shaped upper core layer.

Diapers tested, leakage study and wicking results are shown in Table IV.

TABLE IV

| Diaper Type | Hydrogel in Insert Only | Uniform Hydrogel Distribution |
|---|---|---|
| Cellulose Fiber | 28.6 g | 27.5 g |
| Hydrogel | 4.95 g | 6.13 g |
| Tissue | 2.2 g | 2.3 g |
| Avg. Overall Urine Load (g) | 291 | 282 |
| Avg. Hydrogel Efficiency (g/g) | 29.75 | 24.2 |
| Avg. Length of Dry Core at Back (cm) | 0.76 | 4.62 |

The Table IV data demonstrate the improved efficiency of hydrogel fluid absorption performance which can be realized by placing the hydrogel exclusively in a particular type of smaller insert core positioned toward the front of the diaper. The Table IV data also demonstrate that the hydrogel-free hourglass core tends to provide better wicking performance than a hydrogel-containing hourglass. It should be noted, however, that even though urine wicks further to the back of the hourglass-shaped core in diapers of this invention, there is still substantially no rewet of the skin through the topsheet at the back portion of the diaper. This is so because urine load at the rear of the hourglass is relatively small compared to urine load in the insert.

The diapers of Examples I and II are, in fact, especially effective in capturing discharged urine and holding such urine in the hydrogel-containing lower fluid storage layer of the diaper. There is thus substantially no contact of diapered skin with mixtures of urine and feces. Such separation of urine and feces into different regions of the diaper can provide a significant skin condition benefit in terms of prevention or reduction of the incidence of diaper rash.

EXAMPLES V-IX

Several dual core diaper executions similar to that of Example I are prepared and tested in comparision with a control diaper having hydrogel uniformly distributed in a single hour-glass-shaped core. The dual core diapers all have an upper, hourglass-shaped fluid acquisition/distribution layer which is approximately 38.7 cm long $\times$ 25.4 cm wide (625 cm$^2$ in area) and a tissue-wrapped, oblong fluid-storage, lower insert layer which is approximately 25.4 cm long $\times$ 11.4 cm wide (270.9 cm$^2$ in area). The amounts of cellulose fiber hydrogel in each layer are varied, but in all instances the lower, fluid storage insert layer is positioned toward the front of the diaper such that at least about 90% of the hydrogel material in the insert is found in the front two-thirds section of the diaper and at least about 60% of the hydrogel in the insert is found in the front half of the diaper. The control diaper has a single, tissue-wrapped hour-glass-shaped core which is approximately 38.7 cm long $\times$ 21.6 cm wide (614.2 cm$^2$ in area).

All of these diapers are described in greater detail in Table V. Table V also includes an indication of the relative cost of materials used in the dual-layer core diaper cores vis-a-vis to the cost of materials used in the core of the single core diaper.

TABLE V

| | Example No. | | | | | |
|---|---|---|---|---|---|---|
| | Control | V | VI | VII | VIII | IX |
| | | | Core Type | | | |
| | Uniform Single Layer | D/L | D/L | D/L | D/L | D/L |
| Absorbent Materials | | (upper/lower) | (upper/lower) | (upper/lower) | (upper/lower) | (upper/lower) |
| Cellulose Fiber (gm) | 37.8 | 18.8/10.4 | 23/11.0 | 23.4/11.3 | 19.6/12.3 | 23.5/12.1 |
| Hydrogel* (gm) | 6.13 | 0/4.5 | 1.2/2.3 | /6.3 | 0/3.1 | 0/4.8 |
| Percent Hydrogel in Cellulose (%) | 14.0 | 0/30 | 5/17 | 0/36 | 0/20 | 0/28.4 |
| Tissue (gm) | 2.3 | 0/3.5 | 0/3.5 | 0/4.4 | 0/2.2 | 0/2.2 |
| Basis Weight in Crotch (g/cm$^2$) | 0.10 | 0.033/0.059 | 0.039/0.048 | 0.36/0.060 | 0.030/0.054 | 0.036/0.058 |
| Density in Crotch (g/cm$^3$) | 0.14 | 0.10/0.14 | 0.11/0.12 | 0.11/0.14 | 0.10/0.12 | 0.10/0.13 |
| Relative Absorbent Core Cost (%) | 100 | 81 | 81 | 104 | 72 | 92 |

*The hydrogel is Sanwet IM-1000 marketed by Sanyo Chemical Industries, Inc.
D/L = Dual Layer The single layer and dual layer core diapers of Table V are tested in two types of leakage studies. One such study is of the same general type described in Example III hereinbefore. In addition to providing the overall average urine load at failure and the effective average hydrogel load, such a test also provides measurements of several additional diaper performance parameters. For example, by carefully visually inspecting and by dissecting the diaper at the end of the wearing period, it can be determined whether the diaper core held together and did not tear under the stresses of wearing and loading. It is also possible to determine the percent of urine held by each layer of the diaper, e.g., percent of urine held in the fluid storage layer. Finally, it is possible to determine the extent of wicking provided by the acquisition/distribution layer by measuring how far back the acquisition/distribution layer has been wetted.

In a second type of leakage study, diapers are worn by infants in the home under actual usage conditions. Mothers weigh the test diapers at the time of removal and observe and record the extent to which leakage has occurred. In this manner, it is possible to calculate the percent of diapers in the test that fail up to given loading levels.

Results from these two types of leakage studies are provided in Table VI. The Table VI data represent an average of several tests. Not all types of leakage data are available for every diaper type tested.

TABLE VI

| | | Example No. | | | | |
|---|---|---|---|---|---|---|
| | Control | V | VI | VII | VIII | IX |
| | | | Core Type | | | |
| Preformance Evaluation | Uniform Single Layer | D/L | D/L | D/L | D/L | D/L |
| (1) Leakage Study | | | | | | |
| Avg. Overall Urine Load (g) | 312 | 337 | N/A | 399 | 298 | 343 |
| Avg. Hydrogel Load (g/g) | 21.4 | 44.0 | N/A | 36.7 | 47.4 | 36.9 |
| % Urine Held in Lower Core (%) | — | 81 | N/A | 73 | 70 | 71 |
| Avg. Length of Dry Core at Back (cm) | 8.8 | 0.6 | N/A | 0.79 | 0.25 | 1.8 |
| % Reduction in Diaper Core Tearing Versus Base (Accelerated Usage Conditions) (%) | Base | N/A | N/A | 100 | 93 | 46 |
| (2) Percent Leakage in Home Study (Overnight Use) | | | | | | |
| % of Diapers Failed at Loadings up to 150 g. of Urine (%) | 4.6 | 0.3 | 1.8 | N/A | N/A | 1.3 |
| % of Diapers Failed at Loadings up to 300 g. of Urine (%) | 12.0 | 6.8 | 8.1 | N/A | N/A | 4.6 |

N/A = Not Available
D/L = Dual Layer

The Table VI data illustrate that there are a number of important advantages provided by the diaper constructions utilizing the dual core configuration of this invention. In the first place, it can be seen that the hydrogel is much more efficiently utilized as best indicated by the improved hydrogel load values in comparison with the control. Furthermore, the storage layer contains most of the fluid (e.g., 70–80%) even though it provides less than half of the absorbent weight. This is desirable since fluid stored in this layer is more resistant to release upon pressure. Thus the diapers of the present invention minimize the release of fluid back through the topsheet, thereby keeping the infant's skin drier. It should also be noted that by having most of the fluid held in the fluid storage layer positioned toward the front of the diaper, there is a significantly reduced tendency for urine to mix with feces at the back of the the diaper in contact with the wearer's skin.

The Table VI data also demonstrate that wicking in the dual layer core products is much more efficient as shown by the much smaller dry area at the back of the acquisition/distribution layer of the core. Furthermore, it can be seen that the dual layer core structure has improved resistance to tearing as shown by the percent reduction in diaper tearing versus the base non-layered core product.

Finally the Table VI data show that higher diaper capacity can be obtained at similar relative cost of core material or, alternatively, that approximately equal diaper capacity can be realized for 20–30% less cost in comparison with single uniform core structures due to the more efficient use and placement of the hydrogel material. Even when the dual layer core products are designed to have equal capacity to homogenous core products in a leakage study context, the dual layer design will have fewer leaks in home use because their performance is more reliable as well as more efficient. Such better reliability is best illustrated by the lower percent leakages in the home testing under overnight stress use.

What is claimed is:

1. A disposable absorbent article comprising:
   (A) a liquid impervious, elongated backing sheet;
   (B) a relatively hydrophobic, liquid pervious topsheet; and
   (C) a layered absorbent core positioned between said backing sheet and said topsheet, said core comprising:
      (i) an upper fluid acquisition/distribution layer having a density of from about 0.05 to 0.25 g/cm$^3$ and consisting essentially of hydrophilic fiber material and from 0% to about 8% by weight of said upper layer of particles of substantially water-in-soluble hydrogel material; and
      (ii) a lower fluid storage layer having a density of from about 0.06 to 0.3 g/cm$^3$ and consisting essentially of a substantially uniform combination of hydrophilic fiber material and from about 9% to 60% by weight of said lower layer of particles of substantially water-insoluble hydrogel material;
   said lower fluid storage layer having a top surface area which is from about 0.25 to 1.0 times that of said upper fluid acquisition/distribution layer and said lower fluid storage layer further being positioned relative to said backing sheet and said upper layer in a manner such that at least about 75% of the hydrogel material in said lower layer is found within the front two-thirds section of said absorbent article and such that at least about 55% of the hydrogel material in said lower layer is found within the front half section of said absorbent article.

2. An article according to claim 1 wherein
   (A) the upper fluid acquisition/distribution layer is elongated and has a density which ranges from about 0.07 to 0.14 g/cm$^3$;
   (B) the lower fluid storage layer comprises an intimate admixture of hydrophilic fiber material and hydrogel particles and has a density which ranges from about 0.09 to 0.18 g/cm$^3$;
   (C) the lower fluid storage layer contains from about 15% to 40% by weight of said lower layer of hydrogel material substantially uniformly distributed throughout a hydrophilic fiber matrix;
   (D) the lower fluid storage layer has a top surface area which is from about 0.25 to 0.75 times that of said upper layer; and
   (E) at least about 90% of the hydrogel material in said lower fluid storage layer is found in the front two-thirds section of the absorbent article and at least about 60% of the hydrogel material in the lower fluid storage layer is found in the front half section of the absorbent article.

3. An article according to claim 1 wherein the fluid storage layer comprises a laminate of at least two layers of dispersed hydrogel particles separated by and overwrapped with sheets of hydrophilic fiber material.

4. An article according to claim 1, 2 or 3 wherein the hydrophilic fiber material comprises cellulose fibers and wherein the substantially water-insoluble hydrogel material is selected from hydrolyzed acrylonitrile grafted starch, acrylic acid grafted starch, polyacrylates, isobutylene maleic anhydride co-polymers or mixtures of such hydrogel materials.

5. An article according to claim 4 wherein the upper fluid acquisition/distribution layer is substantially free of hydrogel material.

6. An article according to claim 4 wherein the upper fluid acquisition/distribution layer contains hydrogel particles in an amount up to about 6% by weight of said upper layer.

7. An article according to claim 4 wherein
(A) the upper fluid acquisition/distribution layer has a basis weight of from about 0.015 to 0.1 gm/cm$^2$ and
(B) the lower fluid storage layer has a basis weight of from about 0.02 to 0.12 gm/cm$^2$.

8. A disposable diaper article comprising
(A) a liquid-impervious, elongated backing sheet;
(B) a relatively hydrophobic, liquid pervious topsheet;
(C) a layered absorbent core positioned between said backing sheet and said topsheet, said absorbent core comprising;
(i) an elongated upper fluid acquisition/distribution layer having a density of from about 0.07 to 0.14 g/cm$^3$, consisting essentially of hydrophilic fiber material, and being substantially free of hydrogel material; and
(ii) a lower fluid storage layer having a density of from about 0.09 to 0.18 g/cm$^3$ and consisting essentially of an intimate admixture of hydrophilic fiber material and from about 9% to 60% by weight of said lower layer of particles of substantially water-insoluble hydrogel material; said lower fluid storage layer having a top surface area which is from about 0.25 to 0.75 times that of said upper fluid acquisition/distribution layer and said lower fluid storage layer further being positioned relative to said backing sheet and said upper fluid acquisition/distribution layer in a manner such that at least about 90% of the hydrogel material in said lower layer is found within the front two-thirds section of said diaper article and such that at least about 60% of the hydrogel material in said lower layer is found within the front half section of said diaper article.

9. A diaper article according to claim 8 wherein the hydrophilic fiber material comprises cellulose fibers and wherein the substantially water-insoluble hydrogel material is selected from hydrolyzed acrylonitrile-grafted starch, acrylic acid grafted starch, polyacrylates, isobutylene maleic anhydride co-polymers or mixtures of such hydrogel materials.

10. A diaper article according to claim 8 or 9 wherein
(A) the upper fluid acquisition/distribution layer is generally hourglass-shaped and has a basis weight of from about 0.015 to 0.1 gm/cm$^2$; and
(B) the lower fluid storage layer is generally oblong and has a basis weight of from about 0.02 to 0.12 gm/cm$^2$.

11. A diaper article according to claim 10 wherein said generally oblong lower fluid storage layer/comprises an air laid mixture of cellulose fibers and particles of substantially water-insoluble hydrogel material.

12. A diaper article according to claim 10 wherein the particles of hydrogel in said lower fluid storage layer range in size from about 50 microns to 1 mm and wherein said particles comprise from about 15% to 40% by weight of said lower layer.

13. A disposable diaper article comprising
(A) a liquid-impervious, elongated backing sheet;
(B) a relatively hydrophobic, liquid pervious topsheet; and
(C) a layered absorbent core positioned between said backing sheet and said topsheet, said absorbent core comprising:
(i) an elongated upper fluid acquisition/distribution layer having a density of from about 0.07 to 0.14 g/cm$^3$, and consisting essentially of hydrophilic fiber material and up to about 6% by weight of said upper layer of particles of substantially water-insoluble hydrogel material; and
(ii) a lower fluid storage layer having a density of from about 0.09 to 0.18 g/cm$^3$ and consisting essentially of an intimate admixture of hydrophilic fiber material and from about 15% to 40% by weight of said lower layer of particles of substantially water-insoluble hydrogel material; lower fluid storage layer having a top surface area which is from about 0.25 to 0.75 times that of said upper fluid acquisition/distribution layer and said lower fluid storage layer further being positioned relative to said backing sheet and said upper fluid acquisition/distribution layer in a manner such that at least about 90% of the hydrogel material in said lower layer is found within the front two-thirds section of said diaper article and such that at least about 60% of the hydrogel material in said lower layer is found within the front half section of said diaper article.

14. A diaper article according to claim 13 wherein the hydrophilic fiber material comprises cellulose fibers and wherein the substantially water-insoluble hydrogel material is selected from hydrolyzed acrylonitrile-grafted starch, acrylic acid grafted starch, polyacrylates, isobutylene maleic anhydride co-polymers or mixtures of such hydrogel materials.

15. A diaper article according to claim 13 or 14 wherein
(A) the upper fluid acquisition/distribution layer is generally hourglass-shaped and has a basis weight of from about 0.015 to 0.1 gm/cm$^2$; and
(B) the lower fluid storage layer is generally oblong and has a basis weight of from about 0.02 to 0.12 gm/cm$^2$.

16. A diaper article according to claim 15 wherein said generally oblong lower fluid storage layer comprises an air laid mixture of cellulose fibers and particles of substantially water-insoluble hydrogel material.

17. A diaper article according to claim 15 wherein the particles of hydrogel in said upper and lower layers range in size from about 50 microns to 1 mm.

18. A diaper article according to claim 1, 2, 8 or 13 wherein said lower fluid storage layer is a separate insert layer which is over-wrapped with high wet strength envelope web.

19. A diaper article according to claim 18 wherein the envelope web is tissue and is glue-sprayed to the lower fluid storage insert layer.

20. A disposable diaper article comprising
(A) a liquid-impervious, elongated backing sheet;
(B) a relatively hydrophobic, liquid pervious topsheet;
(C) a layered absorbent core positioned between said backing sheet and said topsheet, said absorbent core comprising;
  (i) an elongated upper fluid acquisition/distribution layer having a density of from about 0.07 to 0.14 g/cm$^2$ and consisting essentially of hydrophilic fiber material and from 0% to about 6% by weight of said upper layer of particles of substantially water-insoluble hydrogel material; and
  (ii) a lower fluid storage layer having a density of from about 0.06 to 0.3 g/cm$^3$ and consisting essentially of a laminate of at least two layers of dispersed particles of substantially water-in-soluble hydrogel material separated by and over-wrapped with sheets of tissue, said hydrogel particles comprising from about 9% to 60% by weight of said lower layer;
said lower fluid storage layer having a top surface area which is from about 0.25 to 0.75 times that of said upper fluid acquisition/distribution layer and said lower fluid storage layer further being positioned relative to said backing sheet and said upper fluid acquisition/distribution layer in a manner such that at least about 90% of the hydrogel material in said lower layer is found within the front two-thirds section of said diaper article and such that at least about 60% of the hydrogel material in said lower layer is found within the front half section of said diaper article.

21. A disposable, dual-layer absorbent core suitable for use in an absorbent article, said absorbent core comprising
(A) an elongated upper fluid acquisition/distribution layer having a density of from about 0.05 to 0.25 g/cm$^3$ and consisting essentially of hydrophilic fiber material and from 0% to about 8% by weight of said upper layer of particles of substantially water-insoluble hydrogel material; and
(B) a lower fluid storage layer having a density of from about 0.06 to 0.3 g/cm$^3$ and consisting essentially of a substantially uniform combination of hydrophilic fiber material and from about 9% to 60% by weight of said lower layer of particles of substantially water-insoluble hydrogel material;
said lower fluid storage layer having a top surface area which is from about 0.25 to 1.0 times that of said upper fluid acquisition/distribution layer and said lower fluid storage layer further being positioned relative to said upper layer in a manner such that at least about 75% of the hydrogel material in said lower layer is found within the front two-thirds section of said absorbent core and such that at least about 55% of the hydrogel material in said lower layer is found within the front half of said absorbent core.

* * * * *

UNITED STATES PATENT AND TRADEMARK OFFICE
CERTIFICATE OF CORRECTION

PATENT NO. : 4,673,402

DATED : June 16, 1987

INVENTOR(S) : Paul T. Weisman, Dawn I. Houghton, Dale A. Gellert

It is certified that error appears in the above-identified patent and that said Letters Patent are hereby corrected as shown below:

Column 1, line 17, "c le" should be --capable--

Column 2, line 15, "4,333,426" should be --4,333,462--

Column 4, line 67, "December 10, 1963" should be --Issued December 10, 1963--

Column 10, line 38, "upper layer 103" should be --104. The upper layer 103--

Column 10, line 39, "layer 104 comprises" should be --layer 104 also comprises--

Column 10, line 43, "positioned" should be --is positioned--

Column 12, line 27, "ca" should be --calculate--

Column 13, line 65, "Example I" should be --Example II--

Column 14, line 2, "625" should be --625.6--

Column 16, line 32, "water-in-soluble" should be --water-insoluble--

Column 18, line 8, "layer/comprises" should be --layer comprises--

Column 19, line 17, "$cm^2$" should be --$cm^3$--

UNITED STATES PATENT AND TRADEMARK OFFICE
CERTIFICATE OF CORRECTION

PATENT NO. : 4,673,402
DATED : June 16, 1987
INVENTOR(S) : Paul T. Weisman et al Page 2 of 2

It is certified that error appears in the above-identified patent and that said Letters Patent is hereby corrected as shown below:

Column 19, line 24, "water-in-soluble" should be --water-insoluble--.

Signed and Sealed this

Nineteenth Day of July, 1988

Attest:

DONALD J. QUIGG

*Attesting Officer*        *Commissioner of Patents and Trademarks*